United States Patent [19]

Budai et al.

[11] Patent Number: 5,652,270
[45] Date of Patent: Jul. 29, 1997

[54] PHARMACEUTICAL COMPOSITIONS CONTAINING BICYCLOHEPTANE ETHER AMINES AND A PROCESS FOR THE PREPARATION THEREOF

[75] Inventors: Zoltán Budai; István Gacsályi; Gábor Szénási; Tibor Mezei; Anikó Kovács; Gábor Blaskó, all of Budapest; Katalin Szemerédi, Budakalász; Gyula Simig, Budpaest; Lujza Petócz, Budapest; Klára Reiter née Esses, Budapest, all of Hungary

[73] Assignee: Egis Gyogyszergyar RT, Budapest, Hungary

[21] Appl. No.: 664,804

[22] Filed: Jun. 17, 1996

Related U.S. Application Data

[63] Continuation-in-part of Ser. No. 498,014, Jul. 3, 1995, abandoned.

[30] Foreign Application Priority Data

Jul. 1, 1994 [HU] Hungary ................ P9401968

[51] Int. Cl.$^6$ ............ A61K 31/54; A61K 31/495; A61K 31/445
[52] U.S. Cl. ............ 514/644; 514/645; 514/657; 514/661
[58] Field of Search ............ 514/644, 645, 514/657, 661

[56] References Cited

U.S. PATENT DOCUMENTS 4,342,762 8/1982 Budai et al. ............ 424/246

*Primary Examiner*—Frederick Krass
*Attorney, Agent, or Firm*—Beveridge, Degrandi, Weilacher & Young, LLP

[57] ABSTRACT

The invention refers to a pharmaceutical composition, a process for the preparation thereof and a novel medical use of bicycloheptane derivatives. The pharmaceutical compositions of the invention comprise a bicycloheptane derivative of the formula I

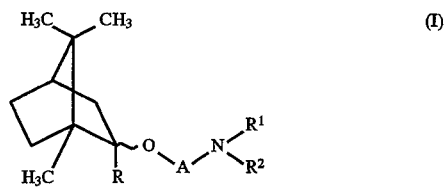

wherein said derivative is as defined in the specification herein. The pharmaceutical compositions of the invention are suitable for the treatment of diseases and disorders that are connected with the influence on the cholecystokinin system, especially for preventing the spastic contraction of the gallbladder.

25 Claims, No Drawings

PHARMACEUTICAL COMPOSITIONS CONTAINING BICYCLOHEPTANE ETHER AMINES AND A PROCESS FOR THE PREPARATION THEREOF

REFERENCE TO A RELATED APPLICATION

This is a continuation-in-part of our U.S. patent application Ser. No. 08/498,014 filed 3 Jul. 1995 and now abandoned which is relied on and incorporated herein by reference in its entirety.

The invention refers to a pharmaceutical composition, a process for the preparation thereof and a novel medical use of bicycloheptane derivatives.

It is known that bicycloheptane derivatives of the formula I

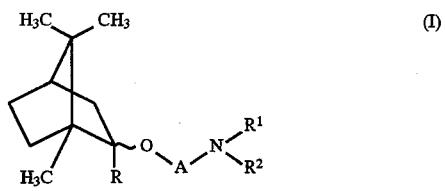

wherein $R^1$ and $R^2$ may be the same or different and represent a $C_{1-5}$ alkyl group or a $C_{3-6}$ cycloalkyl group or they form, together with the adjacent nitrogen atom, a heterocyclic ring containing 4–7 carbon atoms and optionally a further hetero atom e.g. an oxygen, sulfur or nitrogen atom, and this latter may be optionally substituted by a $C_{1-3}$ alkyl, benzyl or phenyl group, R represents a phenyl, phenyl-($C_{1-3}$ alkyl) or thienyl group optionally substituted by one or more halogen or $C_{1-3}$ alkoxy substituent(s), A represents a $C_{2-5}$ straight or branched alkylene chain, and ~ represents a valence bond of ∝ or β configuration. have anticonvulsive, motility inhibiting and analgesic activities, furthermore potentiate the narcosis induced by hexobarbital. In case of certain compounds, the above main activities are supplemented by weak antiserotonin, gastrointestinal peristaltic inhibiting and antiinflammatory effects (U.S. Pat. No. 4,342,762).

The spastic contraction of the cholecyst occurs, in most instances, if in the gallbladder there are gallstones blocking the bile duct. In case of obstruction, the biliary flow is reduced or stopped, the consequence of which is an elevated pressure in the gallbladder leading to a very strong pain.

Cholelithiasis is a disease that occurs frequently, about 10 per cent of the population is affected by it (W. C. Bowman and M. J. Rand, Textbook of Pharmacology, Blackwell Scientific Publications, Oxford, 1980, p. 2610). Three main types of gallstones are distinguished in the literature: gallstones of cholesterol type, pigment type and mixed type. The gallstones of mixed type occur most often. In case of women, the occurrence of gallstones is twice so high than in case of men. Also in persons having overweight, the occurrence of gallstones is more frequent.

In cholelithiasis, the chemotherapy of spastic states is not settled at present since the available drugs do not inhibit the spastic contraction of gallbladder in a selective way.

In general, the surgical intervention (i.e. the removal of the gallstone or cholecyst) is preferred. Chemotherapy includes the administration of nitroglycerol, atropin, analgesics and spasmolytics (J. Knoll, Gyógyszertan, Medicina, Budapest, 1983, p. 372; I. Magyar, Rövid belgyógyászat, Medicina, Budapest, 1985, p. 554; Goodman and Gilman's, The pharmacological basis of therapeutics, Macmillan, New York, 1985, p. 822).

Because of their extremely wide spectrum of effect, atropin and nitroglycerol are rarely employed in practice since a great number of other effects (i.e. side effects) occur, too.

The aim of the invention is to provide pharmaceutical compositions that can be favourably used in the treatment of clinical patterns including the spastic contraction of gallbladder such as bilious attack and biliary colic.

The above aim is achieved by the recognition on which the invention is based as well as by bringing it into practice.

The invention is based on the recognition that the active ingredients of the pharmaceutical compositions of the invention exert their effect through the inhibition of the peripheral cholecystokinin (CCK) system.

Cholecystokinin is released from the secretory cells being at the distal part of duodenum in the mucosa. In the first place, the release of cholecystokinin is caused by the presence of lipids and essential amino acids. Due to the blood circulation, cholecystokinin reaches the cholecyst giving rise to the contraction thereof, thus, the discharge of bile is realized. Relying upon the results of investigations performed on human beings, it seems that, under physiological conditions, CCK is responsible for the discharge of the gallbladder in 80 per cent.

Thus, if the effect of CCK that releases as a consequence of a physiological stimulus can be blocked, then the contraction of the gallbladder can be prevented—and this is the aim of therapy in the present case. Namely, bilious attack can be considered as an extreme contraction (W. C. Bowman and M. J. Rand, Textbook of Pharmacology, Blackwell Scientific Publications, Oxford, 1980, pp. 2520–2521) that is prevented by the receptor antagonists $CCK_A$ (Beglinger et al., Lancet, Vol. 334, No. 8655, 1989, p. 167).

Surprisingly, it was found that the compounds of the formula I inhibit the CCK system.

The invention refers to a process for the preparation of a pharmaceutical composition in which the active ingredient is a bicycloheptane derivative of the formula I wherein R represents a phenyl or a benzyl group;

$R^1$ and $R^2$ stand for a lower alkyl group or one of $R^1$ and $R^2$ is hydrogen and the other is a lower alkyl group; and A denotes a straight or branched chained alkylene group having 2 to 4 carbon atoms;

or N-oxide or optical isomer thereof or a possible mixture of the optical isomers or a pharmaceutically acceptable acid addition salt or quaternary ammonium derivative of the compound of the formula I, its optical isomer or a possible mixture of the optical isomers, said process being characterized by admixing the active ingredient prepared in a manner known per se to conventional pharmaceutical carriers and/or auxiliary materials and forming the mixture obtained into a pharmaceutical composition suitable for the treatment of diseases and disorders that are connected with the influence on the cholecystokinin (CCK) system.

According to a preferred process of the invention, a pharmaceutical composition preventing the spastic contraction of the gallbladder is prepared.

Furthermore, the invention refers to a pharmaceutical composition suitable for the treatment of diseases and disorders connected with the influence on the cholecystokinin (CCK) system, said pharmaceutical composition comprising as the active ingredient a bicycloheptane derivative of the formula I wherein R represents a phenyl or a benzyl group;

$R^1$ and $R^2$ stand for a lower alkyl group or one of $R^1$ and $R^2$ is hydrogen and the other is a lower alkyl group; and A denotes a straight or branched chained alkylene group having 2 to 4 carbon atoms;

or N-oxide or optical isomer thereof or a possible mixture of the optical isomers or a pharmaceutically acceptable acid addition salt or quaternary ammonium derivative of the compound of the formula I, its optical isomer or a possible mixture of the optical isomers and inert solid or liquid pharmaceutical carriers and/or auxiliary materials.

Preferred pharmaceutical compositions of the invention prevent the spastic contraction of the gallbladder.

The pharmaceutical compositions of the invention have the therapeutical advantage that they are able to influence, in a selective manner, the system being in direct connection with the gallbladder, thus, in addition to enhancing the efficaciousness of the therapy, the probability of the appearance of harmful side effects is reduced.

Under the expression used in the description "lower alkyl group" straight or branched chained alkyl groups having 1 to 4 carbon atoms are meant (e.g. methyl, ethyl, n-propyl or isopropyl groups etc.). When $R^1$ and $R^2$ stand for alkyl, preferably they represent methyl groups.

The symbol "A" is preferably an ethylene, propylene or 2-methylpropylene group.

Formula I of the invention includes all possible optical isomers of the bicycloheptane derivatives and any mixtures thereof. The compounds of the formula I can correspond to configurations (1R,2S,4R), (1S,2R,4S) or (1RS,2RS,4RS); a preferred configuration is (1R,2S,4R).

The pharmaceutically acceptable acid addition salts of the compounds of the formula I can be formed with inorganic acids (e.g. hydrogen halides such as hydrochloric acid or hydrogen bromide or sulfuric acid, phosphoric acid or nitric acid etc.) or organic acids (e.g. tartaric acid, succinic acid, malic acid, maleic acid, fumaric acid, citric acid, lactic acid,. methanesulfonic acid or p-toluenesulfonic acid etc.).

The quaternary ammonium derivatives of the compounds of the formula I can be formed by reacting the bicycloheptane derivatives of the formula I with alkyl halides (e.g. methyl, ethyl, n-propyl or isopropyl chloride, bromide or iodide etc.).

Preferred compounds of the formula I are the following bicycloheptane derivatives:

(1R,2S,4R)-(−)-2-benzyl-2-(3'-dimethylaminoproposy)-1,7,7-trimethyl-bicyclo/2.2.1/heptane;

(1R,2S,4R)-(−)-2-benzyl-(2'-methyl-3'-dimethylaminopropoxy)-1,7,7-trimethyl-bicyclo/2.2.1/heptane;

(1RS,2RS,4RS)-2-phenyl-2-(2'-dimethylaminoethoxy)-1,7,7-trimethyl-bicyclo/2.2.1/heptane;

(1S,2R,4S)-(+)-2-phenyl-2-(2'-dimethylaminoethoxy)-1,7,7-trimethyl-bicyclo/2.2.1/heptane or pharmaceutically acceptable acid addition salts thereof.

The following compound of the formula I has especially preferred properties:

(1R,2S,4R)-(−)-2-phenyl-2-(2'-dimethylaminoethoxy)1,7,7-trimethyl-bicyclo/2.2.1/heptane and pharmaceutically acceptable acid addition salt thereof.

From the pharmaceutically acceptable acid addition salts the (E)-2-butenedioates formed with fumaric acid were found to be especially preferred.

The effect of the compounds of the formula I is verified on the following test. Known spasmolytics (drotaverine and papaverine) are employed for comparison. (The above spasmolytics are most often used in the therapeutical practice.)

The tests were performed on male mice from the strain NMRI in groups consisting of 8 to 12 animals. At the beginning of the test, the animals were weighing 20 to 30 g.

The animals were starved for 24 hours before beginning the first treatment, however, they were allowed to consume water ad libitum. The compounds to be tested and the carrier (0.4 per cent solution of methyl cellulose) were administered perorally in a volume of 10 ml/kg.

45 minutes after this treatment, an emulsion of 30 per cent yolk in 0.4 per cent methyl cellulose solution was administered perorally. Each mouse consumed 0.5 ml of the emulsion. The animals of the control group consumed 0.5 ml of the carrier i.e. 0.4 per cent methyl cellulose.

After 15 minutes, cervicalis dislocation was employed, the gallbladders were removed and weighed, one by one. The effect of the compounds tested was given as the inhibition of the cholecyst mass decrease induced by yolk, in percentage. From the effects expressed in percentage, $ID_{50}$ values (i.e. doses causing 50 per cent inhibition) were calculated on the basis of dose versus effect correlations by linear regression (Makovec et. al., Pharm. Res. Com., Vol. 19, No. 1, p. 41, 1987). The results obtained are summarized in the following table:

| Compound tested | $ID_{50}$ p.o. in mg/kg |
| --- | --- |
| Compound "A" | 7.0 |
| Compound "B" | higher than 100 |
| Compound "C" | 10–100 |
| Compound "D" | higher than 100 |
| Compound "E" | 10–100 |
| Compound "F" | 10–100 |
| Compound "G" | 10–100 |
| Drotaverine | higher than 100 |
| Papaverine | higher than 100 |

The compounds tested are given hereinafter: Compound "A":

(1R,2S,4R)-(−)-2-phenyl-2-(2'-dimethylaminoethoxy)-1,7,7-trimethyl-bicyclo/2.2.1/heptane (E)-2-butenedioate; Compound "B":

(1S,2R, 4S)-(+)-2-phenyl-2-(2'-dimethylaminoethoxy)-1,7,7-trimethyl-bicyclo/2.2.1/heptane (E)-2-butenedioate; Compound "C":

(1RS,2RS,4RS)-2-phenyl-2-(2'-dimethylaminoethoxy)-1,7,7-trimethyl-bicyclo/2.2.1/heptane (E)-2-butenedioate; Compound "D":

(1R,2S,4R)-(−)-2-phenyl-2-(2'-dimethylaminoethoxy)-1,7,7-trimethyl-bicyclo/2.2.1/heptane-N-oxide (E)-2-butenedioate; Compound "E":

(1R,2S,4R)-(−)-2-phenyl-2-(2'-methylaminoethoxy)-1,7,7-trimethyl-bicyclo/2.2.1/heptane (E)-2-butenedioate; Compound "F":

(1R,2S,4R)-(−)-2-benzyl-2-(2'-methyl-3-dimethylaminopropoxy)-1,7,7-trimethyl-bicyclo/2.2.1/heptane (E)-2-butenedioate; Compound "G":

(1R,2S,4R)-(−)-2-benzyl-3-(3'-dimethylaminopropoxy)-1,7,7-trimethyl-bicyclo/2.2.1/heptane (E)-2-butenedioate.

From the above comparison it can be seen that, as to activity, the compounds of the formula I reach or even surpass the known spasmolytics used for comparison. Thus, compound "A" inhibits the cholecyst contraction induced by yolk at a dose of as low as 7 mg/kg more efficiently by one order of magnitude than the known spasmolytics used for comparison.

Consequently, bicycloheptane derivatives of the formula I can be effectively used in clinical patterns that include the CCK system as a pathogen factor such as the spastic contraction of gallbladder in the first place, furthermore other clinical patterns, for instance acute pancreatitis.

It is deemed that the spasmolytic mechanism of the compounds of the formula I in the treatment of bilious attacks is different from that of the known spasmolytics. Drugs relieving the spastic state of the smooth muscle are called spasmolytics. The smooth muscle spasmolytics such as papaverine or drotaverine are not able to relieve the spasms of the skeletal muscle.

The compounds of the formula I do not show a direct spasmolytic effect in tests with isolated organs, however, they can relieve the bilious attacks induced experimentally. We explain this contradiction by the fact that the compounds of the formula I influence the CCK system. This effect of the active substances of the invention is novel and surprising for the expert.

The pharmaceutical compositions of the invention can be prepared by conventional methods used in the manufacture of pharmaceutical compositions.

For peroral administration, tablets, enteric-coated tablets, dragées or capsules can be prepared. Such pharmaceutical compositions contain 10 to 100 mg of active ingredient in a unit dosage. Preferably, the above solid pharmaceutical compositions comprise silica or binding agents such as poly(vinylpyrrolidone) or gelatin etc. In addition, lubricants such as magnesium stearate, talc or sodium laurylsulfate can be added to the active ingredient of the tablets.

In case of preparing aqueous suspensions and/or elixirs suitable for oral treatment, the active ingredients can be admixed to different flavouring agents, dyestuffs, emulgators and/or diluents such as water, ethanol, propyleneglycol, glycerol etc.

The tablets of the invention can be manufactured using dry or wet granulation processes. Dragées are prepared by coating the core in a usual manner. For the preparation of capsules, the suitable mixture is filled into hard or soft gelatin capsules.

The pharmaceutical compositions of the invention inhibiting the spastic contraction of the gallbladder are, in general, administered in a dose of 0.25 to 40 mg, preferably 1 to 20 mg, for each kg body weight, in 1 to 3 portions, daily. The actual dosage is determined depending on the activity of the active ingredient, the method of treatment, the state of the patient and other factors, as described by the attending physician.

The daily dose of the compounds of the formula I depends on the conditions of the given case (e.g. the body weight and age of the patient, the severity of the disorder to be treated) and is determined by the physician. The daily dose for an adult patient is, in general, about 1 mg to about 100 mg of the active ingredient.

The invention is further elucidated by the following Examples without restricting the invention to the Examples.

EXAMPLE 1

Tablet containing 25 mg of active ingredient One tablet contains:

| | |
|---|---|
| active ingredient of the formula I | 25.0 mg |
| maize starch | 97.0 mg |
| poly(vinylpyrrolidone) | 75.0 mg |
| magnesium stearate | 3.0 mg |
| | 200.0 mg |

Preparation:

A mixture of the active ingredient and maize starch is granulated by wetting with a 15 per cent aqueous poly(vinylpyrrolidone) solution and drying at 40° to 45 ° C. The granules are dried again, then mixed with magnesium stearate and tabletted. The weight of a tablet is 200.0 mg.

EXAMPLE 2

Dragée containing 25 mg of active ingredient One dragée core contains:

| | |
|---|---|
| active ingredient of the formula I | 25.0 mg |
| maize starch | 245.0 mg |
| gelatin | 8.0 mg |
| talc | 18.0 mg |
| magnesium stearate | 4.0 mg |
| | 300.0 mg |

Preparation:

A mixture of the active ingredient and maize starch is wetted with a 10 per cent aqueous gelatin solution, then granulated by passing it through a sieve, and dried at 40° to 45° C. The dry granules are again passed through a sieve, homogenized with talc and magnesium stearate, and compressed to dragée cores weighing 300.0 mg each.

The dragée cores obtained are coated with a layer consisting of sugar and talc in a manner known per se. The dragées obtained are polished with beeswax.

EXAMPLE 3

Dragée containing 50 mg of active ingredient One dragée core contains:

| | |
|---|---|
| active ingredient of the formula I | 50.0 mg |
| lactose | 94.0 mg |
| poly(vinylpyrrolidone) | 4.0 mg |
| magnesium stearate | 2.0 mg |
| | 150.0 mg |

Preparation:

The granules and dragée cores are prepared as described in Example 2. The weight of a dragée core is 150.0 mg. Then, the cores are coated as given in Example 2 to obtain dragées.

EXAMPLE 4

Gelatin capsule containing 25 mg of active ingredient One capsule contains:

| | |
|---|---|
| active ingredient of the formula I | 25.0 mg |
| maize starch | 265.0 mg |
| Aerosil(R) | 6.0 mg |
| Magnesium stearate | 4.0 mg |
| | 300.0 mg |

Preparation:

The ingredients are homogenized, then filled into gelatin capsules of suitable size.

EXAMPLE 5

Injectable solution containing 25 mg of active ingredient One ampoule contains:
active ingredient of the formula I 25.0 mg in 1 ml of water that was distilled twice.

Antiperistaltic effect of Compound A of the present invention was measured in mice according to the method of Stickney et al. (Arch. Int. Pharmacodyn., (1964), 147:113). It was shown that, compared to the vehicle treated control animals, Compound A of the present invention inhibited intestinal peristalsis by 14.1, 18.0 and 33.8% in oral doses of 10, 30 and 100 mg/kg respectively. On the other hand, Compound A of the present invention inhibited egg yolk induced gall bladder emptying in fasted mice with an $ED_{50}$ of 7 mg/kg, p.o. gall bladder emptying was inhibited by Compound A of the present invention in doses more than an order of magnitude lower than gastrointestinal motility; therefore, inhibition of gall bladder emptying can not be predicted based on the weak inhibitory effect of gastrointestinal motility by Compound A of the present invention.

The inhibition of serotonin-provoked diarrhea by bicycloheptane derivatives was measured by the method described by Woolley et al. (Proc. Soc. Exp. Bio. (1950), 98:367). Compound A of the present invention was an order of magnitude less effective in the above test ($ED_{50}$ of Compound A of the present invention: 76 mg/kg, p.o.; $ED_{50}$ of the reference compound cyproheptadine: 11 mg/kg, p.o.) than its inhibitory effect of gall bladder emptying ($ED_{50}$:7 mg/kg, p.o.). Therefore, based on this weak antiserotonin activity measured in the antidiarrheal test, one can not predict strong inhibition of gall bladder emptying by bicycloheptane derivatives of the present invention.

Further variations and modifications of the foregoing will be apparent to those skilled in the art and such variations and modifications are intended to be encompassed by the claims that are appended hereto.

Hungarian Priority application P9401968 filed on 1 Jul. 1994, and U.S. Pat. No. 4,342,762, are relied on and incorporated by reference in their entirety.

We claim:

1. A method of treating the spastic contraction of gallbladder in a patient in need thereof, comprising administering to said patient an amount effective to treat the spastic contraction of gallbladder of a pharmaceutical composition comprising a pharmaceutically acceptable carrier and a bicycloheptane compound of the formula I

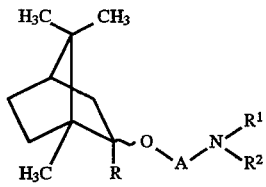

(I)

wherein

R represents a phenyl or benzyl group, $R^1$ and $R^2$ stand for straight or branched chained $C_{1-4}$ alkyl group or one of $R^1$ and $R^2$ is hydrogen and the other is a straight or branched chained $C_{1-4}$ alkyl group, and A denotes a straight or branched chained alkylene group having 2 to 4 carbon atoms; or N-oxide or optical isomer thereof or a mixture of the optical isomers or a pharmaceutically acceptable acid addition salt or quaternary ammonium salt of the compound of the formula I, or optical isomer thereof or a mixture of the optical isomers.

2. The method according to claim 1, wherein said bicycloheptane compound is selected from the group consisting of (1R,2S,4R)-(−)-2-benzyl-2-(3'-dimethylaminopropoxy)-1,7,7-trimethyl-bicyclo/2.2.1/heptane;

(1R,2S,4R)-(−)-2-benzyl-2-(2'-methyl-3'-dimethylaminopropoxy)-1,7,7-trimethyl-bicyclo/2.2.1/heptane;

(1RS,2RS,4RS)-2-phenyl-2-(2'-dimethylaminoethoxy)-1,7,7-trimethyl-bicyclo/2.2.1/heptane;

(1S,2R,4S)-(+)-2-phenyl-2-(2'-dimethylaminoethoxy)-1,7,7-trimethyl-bicyclo/2.2.1/heptane; and pharmaceutically acceptable acid addition salts thereof.

3. The method according to claim 1, wherein said bicycloheptane compound is (1R,2S,4R)-(−)-2-phenyl-2-(2'-dimethylaminoethoxy)-1,7,7-trimethyl-bicyclo/2.2.1/heptane or a pharmaceutically acceptable acid addition salt thereof.

4. The method according to claim 1, wherein said bicycloheptane compound is (1R,2S,4R)-(−)-2-phenyl-2-(2'-dimethylaminoethoxy)-1,7,7-trimethyl-bicyclo/2.2.1/heptane (E)-2-butenedioate.

5. The method according to claim 1, wherein said pharmaceutically acceptable acid addition salt is a (E)-2-butenedioate salt.

6. The method according to claim 1, wherein said administering is oral, rectal or parenteral.

7. The method according to claim 1, wherein said pharmaceutical composition is in the form of a tablet, capsule, dragee, solution, suspension, suppository or injectable solution.

8. The method according to claim 1, wherein said pharmaceutical composition contains 10 to 100 mg of said bicycloheptane compound.

9. The method according to claim 1, wherein $R^1$ and $R^2$ are methyl.

10. The method according to claim 1, wherein A is ethylene, propylene, or 2-methylpropylene.

11. The method according to claim 1, comprising administering 0.25 to 40 mg/kg body weight of said pharmaceutical composition in one to three portions daily.

12. The method according to claim 1, comprising administering a daily dose of 1 to 100 mg of said pharmaceutical composition.

13. A method of inhibiting the release of cholecystokinin in a patient in need thereof comprising administering to said patient an amount effective to at least partially inhibit the release of cholecystokinin of a pharmaceutical composition comprising a pharmaceutically acceptable carrier and a bicycloheptane compound of the formula I

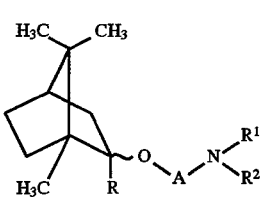

(I)

wherein

R represents a phenyl or benzyl group, $R^1$ and $R^2$ stand for straight or branched chained $C_{1-4}$ alkyl group or one of $R^1$ and $R^2$ is hydrogen and the other is a straight or branched chained $C_{1-4}$ alkyl group, and A denotes a straight or branched chained alkylene group having 2 to 4 carbon atoms; or N-oxide or optical isomer thereof or a mixture of the optical isomers or a pharmaceutically acceptable acid addition salt or quaternary ammonium salt of the compound of the formula I, or optical isomer thereof or a mixture of the optical isomers.

14. The method according to claim 13, wherein said bicycloheptane compound is selected from the group consisting of (1R,2S,4R)-(−)-2-benzyl-2-(3'-dimethylaminopropoxy)-1,7,7-trimethyl-bicyclo/2.2.1/heptane;

(1R,2S,4R)-(−)-2-benzyl-2-(2'-methyl-3'-dimethylaminopropoxy)-1,7,7-trimethyl-bicyclo/2.2.1/heptane;

(1RS,2RS,4RS)-2-phenyl-2-(2'-dimethylaminoethoxy)-1,7,7-trimethyl-bicyclo/2.2.1/heptane; (1S,2R,4S)-(+)-2-phenyl-2-(2'-dimethylaminoethoxy)-1,7,7-trimethyl-bicyclo/2.2.1/heptane; and pharmaceutically acceptable acid addition salts thereof.

15. The method according to claim 13, wherein said bicycloheptane compound is (1R,2S,4R)-(−)-2-phenyl-2-(2'-dimethylaminoethoxy)-1,7,7-trimethyl-bicyclo/2.2.1/heptane or a pharmaceutically acceptable acid addition salt thereof.

16. The method according to claim 13, wherein said bicycloheptane compound is (1R,2S,4R)-(−)-2-phenyl-2-(2'-dimethylaminoethoxy)-1,7,7-trimethyl-bicyclo/2.2.1/heptane (E)-2-butenedioate.

17. The method according to claim 13, wherein said pharmaceutically acceptable acid addition salt is a (E)-2-butenedioate salt.

18. The method according to claim 13, wherein said administering is oral, rectal or parenteral.

19. The method according to claim 13, wherein said pharmaceutical composition is in the form of a tablet, capsule, dragee, solution, suspension, suppository or injectable solution.

20. The method according to claim 13, wherein said pharmaceutical composition contains 10 to 100 mg of said bicycloheptane compound.

21. The method according to claim 13, wherein $R^1$ and $R^2$ are methyl.

22. The method according to claim 13, wherein A is ethylene, propylene, or 2-methylpropylene.

23. The method according to claim 13, comprising administering 0.25 to 40 mg/kg body weight of said pharmaceutical composition in one to three portions daily.

24. The method according to claim 13, comprising administering a daily dose of 1 to 100 mg of said pharmaceutical composition.

25. The method according to claim 13, comprising administering an amount effective to fully inhibit the release of cholecystokinin.

* * * * *